United States Patent
Langer

(10) Patent No.: US 6,921,002 B2
(45) Date of Patent: Jul. 26, 2005

(54) DEVICE FOR DISPENSING ONE- AND MULTI-COMPONENT COMPOUNDS AND VALVE ARRANGEMENT FOR THIS PURPOSE

(75) Inventor: Bernd Langer, Zschopau (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 10/639,786

(22) Filed: Aug. 11, 2003

(65) Prior Publication Data

US 2004/0182882 A1 Sep. 23, 2004

(30) Foreign Application Priority Data

Mar. 21, 2003 (DE) .......................................... 103 12 843

(51) Int. Cl.[7] .................................................. B67D 5/60
(52) U.S. Cl. ............................. 222/145.6; 222/145.5; 222/137; 222/327; 222/504; 366/176.3; 366/177.1
(58) Field of Search ............................. 222/145.5, 334, 222/145.6, 333, 326–327, 386, 389, 136–137, 504; 366/189, 176.3, 177.1, 162.3; 433/90

(56) References Cited

U.S. PATENT DOCUMENTS

| | | | |
|---|---|---|---|
| 3,881,459 A | | 5/1975 | Gaetcke |
| 4,150,769 A | * | 4/1979 | James ......................... 222/137 |
| 4,378,075 A | * | 3/1983 | Voss et al. .................. 222/137 |
| 4,474,310 A | * | 10/1984 | Muller et al. ............. 222/145.5 |
| 4,690,306 A | * | 9/1987 | Staheli ........................ 222/80 |
| 4,693,397 A | * | 9/1987 | Lang .......................... 222/137 |
| 4,976,372 A | * | 12/1990 | Rogers, Jr. .................. 222/324 |
| 5,203,839 A | * | 4/1993 | Skaggs ....................... 222/137 |
| 5,286,105 A | | 2/1994 | Herold et al. |
| 5,411,180 A | * | 5/1995 | Dumelle ..................... 222/137 |
| 5,577,637 A | * | 11/1996 | Voss ........................... 222/137 |
| 5,632,415 A | * | 5/1997 | McGill ........................ 222/95 |
| 5,911,343 A | * | 6/1999 | Keller ..................... 222/145.1 |
| 6,234,795 B1 | * | 5/2001 | Fischer ........................ 433/90 |
| 6,315,164 B1 | | 11/2001 | Mü hlbauer |

FOREIGN PATENT DOCUMENTS

| | | | | |
|---|---|---|---|---|
| DE | 4029193 A1 | * | 5/1991 | ............ B29B/7/76 |
| DE | 39 20 694 A1 | | 10/1991 | |
| EP | 492 413 A1 | | 12/1991 | |
| EP | 0 787 515 A1 | | 1/1997 | |
| EP | 1 010 401 A1 | | 11/1998 | |
| EP | 1 101 638 A2 | | 10/2000 | |

* cited by examiner

Primary Examiner—Frederick C. Nicolas
(74) Attorney, Agent, or Firm—Collard & Roe, P.C.

(57) ABSTRACT

A device for mixing and metering one or multi-component compounds from at least one cartridge. These compounds can be in the form of a basic component and a catalyst component for impression compounds for dental applications. This device includes a punch for admitting pressure to the cartridge. This punch is supported in a displaceable manner, and is associated with each cartridge. This device also includes a hydraulic circuit which is associated with said at least one punch so that it actuates a piston or a cylinder of a hydraulically actuated piston cylinder unit. This device includes at least one pump and a supply container. This invention also includes a valve arrangement for this device.

22 Claims, 3 Drawing Sheets

DEVICE FOR DISPENSING ONE- AND MULTI-COMPONENT COMPOUNDS AND VALVE ARRANGEMENT FOR THIS PURPOSE

CROSS REFERENCE TO RELATED APPLICATIONS

Applicant claims priority under 35 U.S.C. §119 of German Application No. 103 12 843.3 filed Mar. 21, 2003.

BACKGROUND OF THE INVENTION

The invention relates to a device for dispensing either one component or multi-component compounds from at least one cartridge. This device includes a punch that is supported in a displaceable manner which is associated with each cartridge and is used to apply pressure to the cartridge. These devices are used as metering and mixing devices for dispensing a basic component and a catalyst component. These components are mixed with each other to form a compound for producing impressions in the dental field.

The cartridges are formed as hose like pouches that are emptied by the pressure applied by the punches, so that the components discharged into the mixer are blended in this mixer to obtain a compound that is ready to be used for impressions. In addition, this invention relates to a valve arrangement that can be used with this type of a device.

Devices for dispensing compounds are known in the art. For example, European Patent No. EP 492 413 A1 discloses two plungers that can be displaced from cartridges for mixing and dispensing two-component compounds. These plungers are jointly driven by an electric motor via a magnetic clutch and a chain drive. At the same time, this motor is rotationally driving a shaft which is connected to the mixer to intimately blend the components with each other.

In addition, a dispensing device for cartridges is also known from the art. For example, European Patent No. EP 1 101 638 A2 discloses a set of tappet plates that can be displaced with a carriage by means of an electromechanical driving system and threaded spindles. In addition, a device for dispensing a multi-component compound is also disclosed by European Patent No. EP 1 010 401 A1. With this device, the punch acts on cartridges that can be driven by an electric motor via a threaded spindle.

Furthermore, European patent No. EP 787 515 B discloses a dispensing device for dispensing at least two components. This device comprises a metering cylinder with a feeding plunger for each component. This device also includes a drive unit that is actuated either electrically, pneumatically, or by hand for operating this device.

After these devices have been shut off, the drive of the plungers should come to a standstill immediately to prevent the feed of the two components that are to be mixed with each other. Thus, this feeding will not continue, so that the dispensed compound can be exactly metered out and so that it is not contaminated by flowing back into a mixer and thus, these components will not set back in the mixer.

To control this flow, and prevent the setting of these components in the mixer, European Patent No. 492 413 A1 uses a magnetic clutch that can be engaged and disengaged when the motor drive of the plunger is switched on and off. With this design, the plungers are connected with the motor drive via this magnetic clutch. Thus, this structure for applying single- or multi-component compounds is made very complicated and therefore, the manufacture of this type of a device is very expensive. Additionally, many components required for the drive of these plungers are subject to repair. The operating costs of these plungers is high as a consequence of the required maintenance and repair work.

In addition, another drawback with some of the known devices listed above is that it is possible that after the drive has been shut off, one of the components may flow from a first cartridge into a mixer or into a second cartridge, where it will mix with the other compound received there. When the components comprise a basic component and a catalyst component, these components cure in the mixer so that this mixer gets clogged and becomes unstable.

Therefore, the problem of the invention is to provide a device which can exactly meter out components with a high volume output of dispensed material, wherein this device requires a low amount of repair work, and wherein this device can be manufactured with a minimal number of components, in a compact way, and at a favorable cost.

In addition, another problem of the invention is to provide a valve arrangement with a high volume opening that can be opened with low setting forces even at high pressure.

SUMMARY OF THE INVENTION

To resolve the above problems associated with the references discussed, the invention relates to a device for metering out compounds that has a hydraulic system or circuit in communication with at least one punch for actuating a piston or a cylinder of a hydraulically actuated piston-cylinder unit. This hydraulically actuated piston cylinder unit comprises at least one pump and at least one supply container or reservoir.

By using a hydraulically actuated piston-and-cylinder unit, wherein at least one piston is displaced in the device, it is possible to have particularly exact metering of the compounds that are dispensed. This is because the pressure that is hydraulically applied to the one or more plungers or pistons can be built up quickly and also reduced again rapidly after the device has been switched off. In addition, it is also possible to omit the toothed racks, chain drives, toothed gear drives, spindles or similar devices which are usually required with these type devices for translating a rotational movement of a drive shaft into a linear or axial movement of a piston. Thus, this means that the device can be built with a more compact structure and with fewer components which allows a reduction in the manufacturing costs.

In addition, at the same time, this hydraulically actuated piston and cylinder unit operates almost free of maintenance and with a low susceptibility to repair.

With a device having a plurality of cartridges and pistons, it is possible to have or to allocate a piston- and cylinder unit to each punch. Such a unit may be actuated by hand, so that the components can be dispensed from the cartridges with a dispensation volume that can be adjusted to an exact amount or level. In this way, the adjustable dispensation volume permits different mixing ratios that can be adjusted in a defined manner for each cartridge.

In a preferred embodiment of the invention, at least one of the punches is a piston, or a cylinder of a hydraulically actuated piston-cylinder unit.

This device can be manufactured in a particularly space saving way because at least one of the punches serves as a piston or cylinder of the piston cylinder unit and at the same time as a punch that is acting on the cartridges. In addition, the number of components required for building the device can be further reduced so that it is simpler in design.

This punch can be formed as a cylindrical tube that is closed on the side facing the cartridges. This type of tube can be displaced as a cylinder moving in a fixed piston. This cylinder is consequently sliding in a fixed piston so that the required length of the device corresponds with only the length of the extended piston and cylinder unit. This type of an arrangement of the cylinder with a plunger, without a piston rod to which a pressure medium is admitted only on one side, is called a plunger-cylinder.

If the plunger is designed to form a hollow plunger, this type if device can serve as a reservoir in the hydraulic circuit. Thus, it is not necessary to create a separate supply container for oil or some other type of suitable hydraulic fluid. This structure of the device as defined by the invention is thus simplified, so that the space required for this type of construction can also be reduced.

In another preferred embodiment of the invention, the piston-cylinder unit comprises a hollow plunger so that on the side facing the punch, there is a valve comprising a valve disk. This valve disk can be positioned in a sealing manner against a first valve seat and against the force of at least one spring by means of the pressure in the fluid contained in the cylinder. When the pump is actuated, the pressure of the fluid in the cylinder builds up, automatically closing the valve in the first valve disk, which is pressed in a sealing manner against the valve seat against the force of the spring. A control system that would require an additional expense for a closing valve can be avoided with this arrangement.

The first valve seat and the first valve disk can be penetrated by a bar on which a second smaller valve disk is formed on its end facing the cylinder. Via the pressure of the fluid in the cylinder, this second valve disk can be driven and placed in a sealing manner against a second valve seat that is in the first larger valve disk. This bar which supports the second valve disk, permits a quick relief of the pressure of the fluid in the cylinder after the pump has been switched off. The second, smaller valve disk is detached from the second valve seat via the bar, so that the fluid can drain through the first valve disk from the cylinder into the hollow plunger. When the pressure of the fluid in the cylinder has been relieved, the first larger valve disk is lifted from the valve seat by the springs applying a force. Thus, the fluid can now flow from the cylinder into the hollow plunger with a high flow volume.

Alternatively, the pressure of the fluid can be relieved from the cylinder after the pump has been shut off by providing the pump with a defined leakage of 0.2 ml/s. When this pump has been shut off, a portion of the hydraulic fluid can then flow through the pump and back into the reservoir. This leakage lowers the pressure of the fluid in the cylinder so that the first valve disk will be lifted from the first valve seat by the force of the at least one spring. Thus, the fluid can also flow through the valve from the cylinder into the supply container with a high flow volume.

The first valve seat can be formed as a cap that comprises at least one opening that can be closed by the first valve seat, and a second, smaller opening for feeding fluid from the pump into the cylinder. With this embodiment, the hollow plunger serves as both a supply container for the hydraulic fluid and also as a location for the extension of the pressure line from the pump to the cylinder. Thus, this structure can be further simplified to reduce the space required for construction.

For an exact metering of the compounds, the device can have two punches that have the same or substantially the same length but different diameters. These two punches are supported in parallel with each other in a displaceable manner in a common plunger-cylinder unit. These two punches are preferably connected with a carriage or bracket that is supported in a displaceable manner on at least one rail. Thus, these two punches are guided on the rails via the carriage in parallel with each other, so that any canting or deviation of the punches is avoided. In addition, with this design, the cylinder does not need any special guidance on the hollow plunger because the cylinder is guided via the carriage. This type of guidance of the punches on the carriage reduces the friction of the punches and the friction of the plunger-cylinder unit as well.

To exchange or replace the cartridges, the punches may need to be moved rapidly from an extended position of the plunger-cylinder unit into a retracted position. A hand wheel can be used to displace or move the carriage by hand. In addition, the punches can also be displaced by using a hand wheel coupled with a pinion that can engage a toothed rack. Consequently, the carriage with the punches can be moved by both turning the hand wheel along with the toothed rack and by driving it manually when the pinion is disengaged from the toothed rack. Thus, the pinion can then be supported either in a stationary manner on a frame or similar device, while the toothed rack is being displaced together with the punches in relation to the stationary toothed rack.

The components that are dispensed from the device, are preferably blended in a mixer or spout that can be driven via a shaft of the mixer. This shaft can be connected with a motor, such as a device that drives a toothed belt that is driving the pump as well.

In another embodiment of the invention, the shaft driving the mixer is supported in a manner substantially parallel with the axis of rotation of the mixer. On the side facing the mixer, this shaft supports a toothed gear that can engage a pinion that is disposed on the mixer in a detachable manner.

The replacement of cartridges and the mixer can be assisted by retracting the shaft from a position in which the shaft engages the mixer, via a release mechanism, when the motor is not operating. The motor, the release mechanism, and the bar supporting the second valve disk can be jointly actuated via a switch. This switch makes it possible to simultaneously switch on the motor that is driving the pump and the shaft, actuate the release mechanism to engage the shaft of the mixer, and move the bar into a position. This causes the second valve disk to be retained in a sealing manner on the second valve seat in the first valve disk, so that a pressure of the fluid in the cylinder is built up. However, it is also possible by using the switch to shut the motor down, to disengage the shaft from the mixer, and to detach the second valve disk from the second valve seat, so that the pressure of the fluid in the cylinder is relieved and the first valve disk is lifted from the valve seat.

If the plunger-cylinder unit has a double-action cylinder, it is also possible to displace the carriage with the punches by driving it hydraulically in both directions. It is also possible to drive the carriage at different speeds.

In addition, this invention relates to a valve arrangement that is suited for controlling a plunger-cylinder unit in a device of the type specified above. This valve arrangement comprises a first, larger opening that comprises a first valve seat, and wherein this device can be closed in a sealing manner by a first, larger valve disk. In this case, the first valve disk can have a second smaller opening that comprises a second valve seat, and wherein this second valve seat can be closed in a sealing manner by a second smaller valve disk. This first valve seat can be moved into its position wherein it is lifted from the first valve seat via at least one pressure spring. Thus, it is possible to detach the second valve disk from its valve seat with relatively low force even if the pressure acting on the valve disk is high. A rapid pressure relief is thus achieved, so that the first valve disk can be easily lifted from its valve seat. Consequently, a high volume of flow can be passed through the first opening of this valve arrangement without having the opening of the valve arrangement impaired by the high forces acting on the first valve disk.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF THE INVENTION

Figure 1:
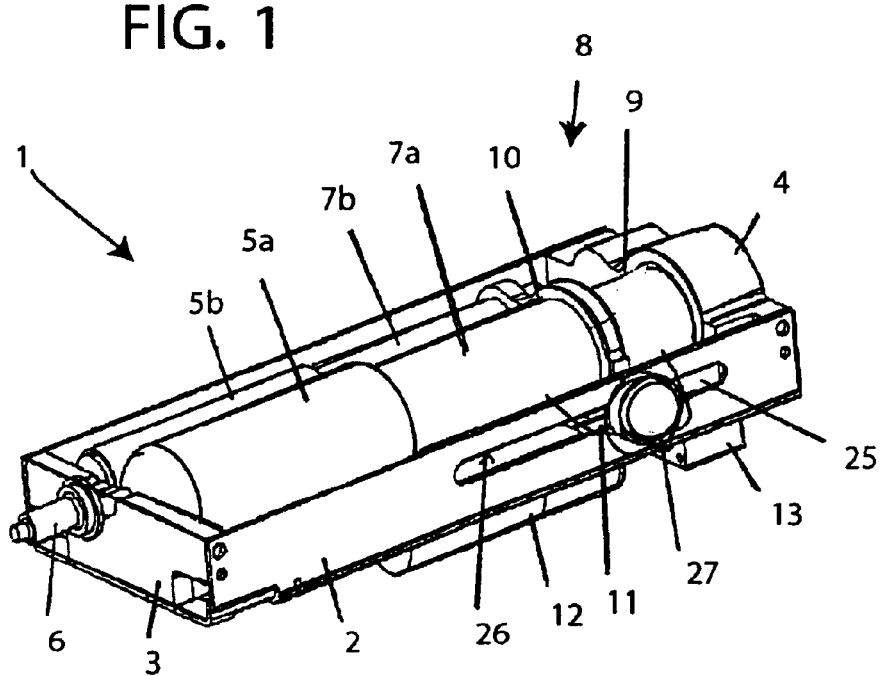
FIG. 1 is a schematic perspective view of the device according to the invention.

Referring now to the drawings, FIG. 1 shows a device 1 for dispensing two components, for example, a basic component and a catalyst component for dental impression compounds. Device 1 comprises a U-shaped frame 2 that is connected on two opposite ends with an abutment or end plate 3 and a plunger plate or piston plate 4. In the area of device 1 facing abutment 3, two cartridges cylindrical chambers or feeding tubes 5a and 5b are disposed in frame 2 and extend through abutment 3, as shown in FIG. 1. Hose-like (or tubular) pouches that contain, for example, a basic component and a catalyst component for producing impression compounds for dental application, can be disposed in these cartridges. In the area of the abutment 3, cartridges 5a and 5b have dispensing openings that, in the present embodiment, feed into a dynamic mixer or spout 6. Dynamic mixer 6 allows the components to thoroughly mixed and discharged from device 1.

To dispense the components from cartridges 5a and 5b, punches, cylinders or pushers 7a and 7b, respectively, are associated with each cartridge for squeezing out the components. These punches 7a and 7b are insertable in cartridges 5a and 5b. To actuate punches 7a and 7b, device 1 can include a piston-cylinder unit 8 formed by a hollow plunger or piston 9, which is connected with piston plate 4 in a fixed manner, and punch 7a that serves as the cylinder. The two punches 7a and 7b are connected to each other in a fixed way via carriage or bracket 10, so that punches 7a and 7b can be jointly displaced in frame 2 in parallel with one another. For this purpose, frame 2 has rails 11 on which carriage 10 slides. Alternatively, each punch 7a, and 7b can have a separate piston-cylinder unit 8 to actuate punches 7a and 7b independently of each other.

A geared motor 12 driving pump 13 is arranged on the side of the U-shaped frame 2 shown as the bottom side in FIG. 1. The suction line of pump 13 is connected with the interior of piston 9 which is formed as a hollow piston. Thus, this piston serves at the same time as a reservoir for hydraulic fluid. The pressure line of pump 13 extends through hollow piston 9 and feeds into punch 7a on the side of hollow piston 9 that faces mixer 6. Punch 7a serves as the cylinder of piston-cylinder unit 8.

Figure 3:
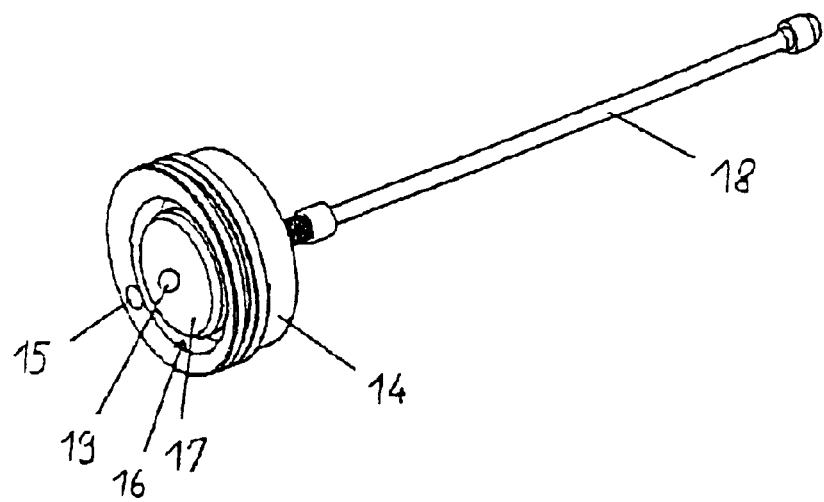
FIG. 3 is a schematic perspective view of the valve arrangement as defined by the invention.
Figure 5:
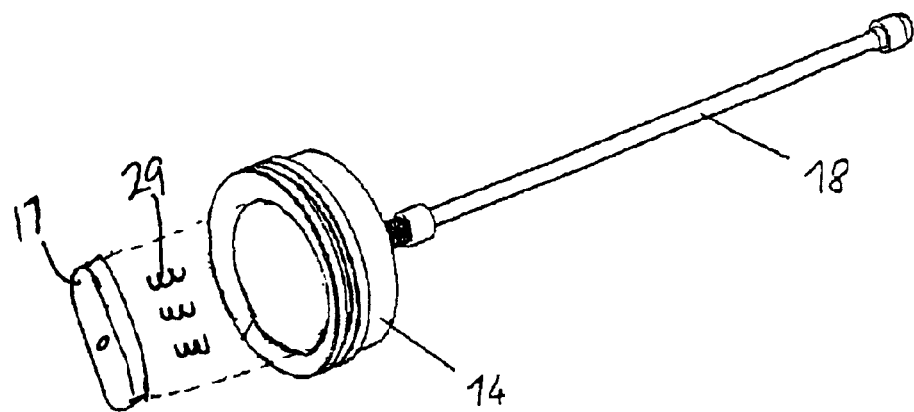
FIG. 5 is a partially exploded view of the valve arrangement shown in FIG. 3.

The side of hollow piston 9 that faces mixer 6 is closed versus the cylinder (punch) by a cap 14 with a double valve. This cap is shown in FIG. 3. Cap 14 has a small opening 15, into which a pressure line (riot shown) of the pump 13 feeds into. Furthermore, cap 14 is has a larger opening 16 that can be closed in a sealable manner by pressing a first, larger valve disk 17 against a first valve seat in cap 14. A plurality of pressure springs 29 are shown in FIG. 5 which shows an exploded drawing of FIG. 3. These pressure springs 29 are arranged between valve disk 17 and cap 14. These pressure springs 29 retain valve disk 17 in a position that is removed from the valve seat in cap 14, so that a fluid can pass through opening 16 in cap 14.

Cap 14 and the first, larger valve disk 17 are penetrated by a bar 18. The bar can have a second, smaller valve disk 19 on the side of the bar shown in FIG. 3. Via bar 18, second valve disk 19 can be displaced into an open position from the closed position shown in FIG. 3, wherein second valve disk 19 is pressed in a sealable manner against a valve seat formed in first valve disk 17. In this open position, second valve disk 19 is lifted from the second valve seat in first valve disk 17. It is then possible for a fluid to flow through first valve disk 17 from cylinder 7a and hollow plunger 9. The two valve disks 17 and 19 thus form a double valve.

Figure 2:
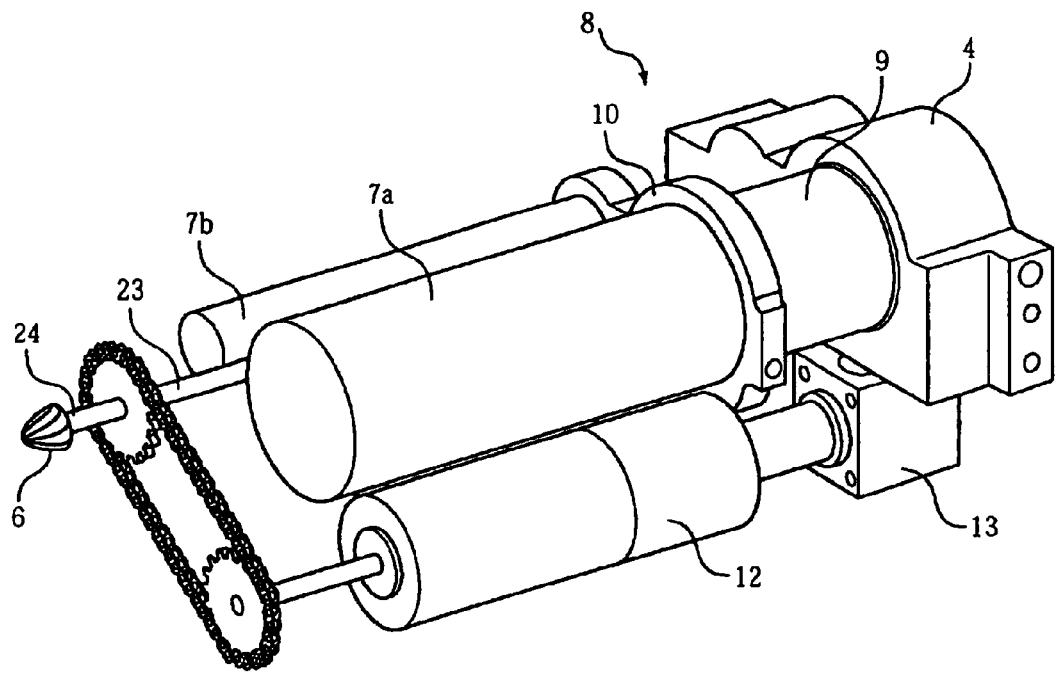
FIG. 2 is a schematic perspective view of the components of the hydraulic circuit according to FIG. 1.
Figure 4:
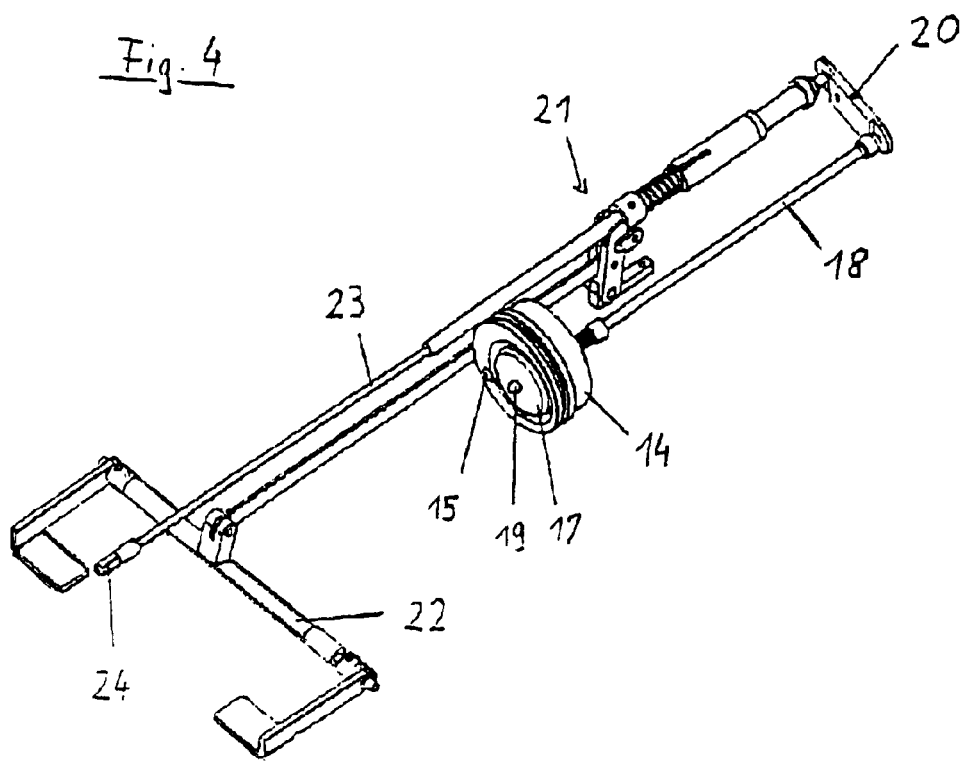
FIG. 4 is a schematic perspective view of the valve according to FIG. 3 with an actuating device.

FIG. 4 shows on the side facing away from second valve disk 19, bar 18 which is connected with a rocker arm 20 that can pivot via a release device 21. This release device can be actuated by a switching shaft 22. A shaft 23 of the mixer can be oppositely displaced in relation to bar 18 in an axial direction. Mixer shaft 23 can be driven by motor 12 via a driving means (See FIG. 2). This driving means can be, for example by a driving means such as a toothed belt, a chain or a similar drive means, and engages mixer 6 with its end 24 located on the side of the mixer when bar 18 presses second valve disk 19 against the second valve seat in the first valve disk 17 via rocker arm 20. As an alternative to the embodiment shown, shaft 23 of the mixer can be supported substantially in parallel with the axis of rotation of mixer 6. Mixer shaft 23 has a toothed gear that can be engaged with a pinion of mixer 6. When mixer 6 is mounted in device 1, this mixer is automatically connected with the shaft of the mixer via a toothed gear and pinion.

Furthermore, in U-shaped frame 2, there is a lateral slot-like window 25 that has a toothed rack 26 on its side shown in FIG. 1 as the upper side. A hand wheel 27 is associated with carriage 10 supporting punches 7a and 7b. This hand wheel is connected with a pinion (not shown). This pinion can be engaged with toothed rack 26 in side window 25, so that the carriage with punches 7a and 7b can be displaced along the toothed rack 26 by turning hand wheel 27. When the pinion is disengaged from the toothed rack, carriage 10 can be freely displaced on rails 11 via hand wheel 27.

The function of device 1 is explained below in greater detail. To dispense a compound for producing dental impressions from cartridges 5a and 5b containing a basic component and a catalyst component, cartridges are jointly inserted in device 1 which serves as a mixing and metering device. Punches 7a and 7b are retracted so that carriage 10 is disposed close to piston plate 4. Shaft 23 of the mixer is in a position in which it is retracted in the direction of piston plate 4, so that cartridges 5a and 5b and mixer 6 can be jointly inserted in device 1.

Punches 7a and 7b associated with cartridges 5a and 5b, respectively, are now jointly inserted in cartridges 5a and 5b via carriage 10. This can be accomplished either by turning hand wheel 27, whereby the pinion connected with hand wheel 27 engages toothed rack 26 of side window 25, or by displacing carriage 10 if the pinion is disengaged from toothed rack 26. Thus, it is possible also to drive punches 7a and 7b into the cartridges by actuating plunger-cylinder unit 8. To achieve this result, the switching shaft 22 is actuated, so that mixer shaft 23 is driven into mixer 6 with its end 24 located on the side of the mixer, and wherein bar 18 is retracted at the same time in the direction of piston plate 4, so that second valve disk 19 is pressed against the second valve seat in first valve disk 17 in a sealing manner. Motor 12, which drives pump 13 and mixer shaft 23, is simultaneously switched on by such actuation of switching shaft 22.

A hydraulic fluid, for example oil or a similar type fluid can flow from hollow plunger 9 serving as the reservoir, through pump 13 and via opening 15 in cap 14 into cylinder 7a. The fluid flowing into cylinder 7a causes a pressure to build up in cylinder 7a, so that first valve disk 17 is pressed in a sealable manner against the first valve seat in cap 14 against the force of springs arranged between said first valve disk and cap 14. By having a rising pressure of the fluid in cylinder 7a, it moves in relation to hollow plunger 9 in the direction pointing away from piston plate 4, so that carriage 10 with two punches 7a and 7b are inserted in cartridges 5a and 5b, respectively, for dispensing the components.

To switch off device 1, switching shaft 22 is pivoted in the opposite direction, so that mixer shaft 23 is engaged from mixer 6 and the motor is stopped. Bar 18 is moved at the same time in the direction of mixer 6, so that second valve disk 19 is lifted from its valve seat in first valve disk 17. The pressure of the fluid in cylinder 7a can be rapidly relived, so that also first valve disk 17 is lifted from its valve seat in cap 14 by the force, which can be generated by springs, which are disposed between valve disk 17 and cap 14. Thus, the fluid can flow back from cylinder 7a into hollow plunger 9. The pressure of the fluid in cylinder 7a is reduced so rapidly that any continuing flow of the components from cartridges 5a and 5b into mixer 6 is avoided. Consequently, no contamination of the components in the cartridges can occur.

To replace cartridges 5a and 5b, punches 7a and 7b can be retracted from the cartridges in the direction of piston plate 4 when motor 12 and driving pump 13 are switched off and second valve disk 19 is lifted from its valve seat in first valve disk 17. Punches 7a and 7b can be displaced either by turning hand wheel 27, if the pinion connected with hand wheel 27 engages toothed rack 26, or by displacing carriage 10 on rails 11, if the pinion is disengaged from toothed rack 26. When second valve disk 19 is in this position, the hydraulic fluid can flow through the opening in first valve disk 17. This opening is penetrated by bar 18, and, if first valve disk 17 is lifted off its valve seat in cap 14, it can flow back into hollow plunger 9 through cap 4 as well. Carriage 10 with punches 7a and 7b can therefore be displaced in both directions in a particularly smooth way.

As an alternative to the manual retraction of carriage 10 with punches 7a and 7b, it is possible to also hydraulically drive carriage 10 out of cartridges 5a and 5b if plunger-cylinder unit 8 has a double-action cylinder (not shown). In addition, it is possible via the control of the delivery of the pump to displace carriage 10 with punches 7a and 7b on rails 11 at different speeds, for example at a high forward and/or rearward speed, and at a slower speed of the operating lift.

Accordingly, while at least one embodiment of the present invention have been shown and described, it is to be understood that many changes and modifications may be made thereunto without departing from the spirit and scope of the invention as defined in the appended claims.

| List of Reference Numerals and Letters | |
|---|---|
| 1 | Device |
| 2 | U-shaped frame |
| 3 | Abutment/endplate |
| 4 | Piston plate/plunger plate |
| 5a, 5b | Cartridge/cylindrical chambers/feeding tubes |
| 6 | Mixer/spout |
| 7a | Punch/cylinder/pusher |
| 7b | Punch |
| 8 | Piston-cylinder unit |
| 9 | Hollow plunger/piston |
| 10 | Carriage/bracket |
| 11 | Rail/guide |
| 12 | Motor/drive |
| 13 | Pump |
| 14 | Cap/cover |
| 15 | Smaller opening |
| 16 | Larger opening |
| 17 | First valve disk/first valve cover |
| 18 | Bar/shaft |
| 19 | Second valve disk/second valve cover |
| 20 | Rocker arm |
| 21 | Disengaging device/release device |
| 22 | Switching shaft |
| 23 | Shaft of mixer |
| 24 | End on side of mixer |
| 25 | Side window/opening |
| 26 | Toothed rack |
| 27 | Hand wheel |

What is claimed is:

1. A device for dispensing a plurality of compounds including a basic component and a catalyst component of impression compounds for application in a dental field comprising:
   a) at least one frame;
   b) at least one cartridge, disposed on said at least one frame;
   c) a plunger-cylinder unit disposed in said frame and comprising:
      i) at least one punch displaceably supported in said at least one frame and coupled to said at least one cartridge; and
      ii) at least one plunger coupled to said at least one punch for providing pressure to said at least one punch;
   d) a hydraulic system for actuating said at least one plunger and said at least one punch;
   e) at least one pump coupled to said frame and in fluid communication with said plunger-cylinder unit; and
   f) a motor coupled to said pump wherein said pump is driven by said motor;
   g) a shaft, wherein said shaft is connected to a mixer and driven by said motor;
   h) at least one supply container in communication with said at least one pump wherein said hydraulic system actuates said at least one pump to cause fluid from said supply container to flow into said at least one plunger to cause said at least one plunger to drive said at least one punch to dispense said plurality of compounds.

2. The device as in claim 1, wherein said at least one cartridge comprises at least two cartridges, and wherein said at least one punch comprises at least two punches, wherein said at least two cartridges and said at least two punches are actuated independently of each other.

3. The device as in claim 2, wherein at least one of said at least two punches, is in a form of a plunger and is associated with said plunger-cylinder unit.

4. The device as in claim 1, wherein said at least one punch is formed by a cylindrical tube closed on one side facing said at least one cartridge.

5. The device as in claim 4, wherein said at least one plunger is a hollow piston and wherein said hollow piston is a supply container in a hydraulic circuit of said piston cylinder unit.

6. The device as in claim 5, wherein said piston cylinder unit further comprises at least one valve, wherein said at least one valve comprises a first valve disk, a first valve seat, and at least one spring, wherein said first valve disk can be placed against said first valve seat in a sealing manner against a force from said spring created by a pressure of a fluid in said cylinder.

7. The device as in claim 6, further comprising a bar, wherein said first valve seat and said first valve disk are penetrated by said bar, and wherein the device further comprises a second valve disk and a second valve seat, disposed in said first valve disk with said second valve disk being placeable in a sealing manner against a second valve seat, wherein said second valve seat is disposed on said first valve disk by a pressure of a fluid in said cylinder.

8. The device as in claim 7, wherein said at least one pump can be placed in a switched off state so that it leaks up to 0.2 ml/s.

9. The device as in claim 6, wherein said first valve disk is formed as a cap having at least one opening that is closable on said first valve disk and a second smaller opening for feeding fluid from said at least one pump into at least one of said at least to punches.

10. The device as in claim 2, wherein said at least two punches have a same length, but different diameters supported in parallel with each other and are displaceable by a common plunger-cylinder unit.

11. The device as in claim 10, further comprising a carriage, and at least one rail, wherein said at least two punches are connected with said carriage, and wherein said carriage is displaceably supported on said at least one rail.

12. The device as in claim 11, further comprising at least one hand wheel, wherein said at least one hand wheel is associated with said carriage for manually displacing said carriage.

13. The device as in claim 12, further comprising a pinion, and a toothed rack wherein said at least one hand wheel can be coupled to said pinion which can engage said toothed rack wherein said hand wheel is for displacing said carriage.

14. The device as in claim 1, wherein said shaft, driving said mixer, is substantially supported in parallel with an axis of rotation of said mixer, and supported on its end on a side of said mixer, the device further comprising a toothed gear, and a pinion detachably coupled to said mixer, wherein said toothed gear is capable of being engaged with said pinion.

15. The device as in claim 1, further comprising a release device, wherein said shaft is retracted via said release device from a position in which it engages said mixer when said motor is not actuated.

16. The device as in claim 15, further comprising a bar, wherein said motor, said release device and said bar supporting said second valve disk can be jointly actuated via a switch.

17. The device as in claim 1, wherein said piston cylinder unit comprises a double-action cylinder.

18. The device as in claim 6, wherein said at least one valve includes a valve arrangement comprising:
   a) a first larger opening forming a first valve seat;
   b) a valve disk for opening and closing said first larger opening;
   c) a second smaller opening forming a second valve seat; and
   d) a second smaller valve disk for closing in a sealing manner said second smaller opening.

19. The valve arrangement as in claim 18, further comprising at least one pressure spring, wherein said first valve disk is acted upon by said at least one pressure spring which moves said first valve disk into position wherein it is lifted from said first valve seat.

20. The valve arrangement according to claim 18, further comprising a bar, wherein said bar can lift said second valve disk from said second valve seat.

21. A device for dispensing a plurality of compounds including a basic component and a catalyst component of impression compounds for application in a dental field comprising:
   a) at least one frame;
   b) at least one cartridge, disposed on said at least one frame;
   c) a plunger-cylinder unit disposed in said frame and comprising:
      i) at least one punch displaceably supported in said at least one frame and coupled to said at least one cartridge wherein said at least one punch is formed by a cylindrical tube closed on one side facing said at least one cartridge; and
      ii) at least one plunger coupled to said at least one punch for providing pressure to said at least one punch wherein said at least one plunger is a hollow piston and wherein said hollow piston is a supply container in a hydraulic circuit of said plunger cylinder unit;
      iii) at least one valve, wherein said at least one valve comprises a first valve disk, a first valve seat, and at least one spring, wherein said first valve disk can be placed against said first valve seat in a sealing manner against a force from said spring created by a pressure of a fluid in said cylinder;
   d) a hydraulic system for actuating said at least one plunger and said at least one punch;
   e) at least one pump coupled to said frame and in fluid communication with said plunger-cylinder unit; and
   g) at least one supply container in communication with said at least one pump wherein said hydraulic system actuates said at least one pump to cause fluid from said supply container to flow into said at least one plunger to cause said at least one plunger to drive said at least one punch to dispense said plurality of compounds.

22. A device for dispensing a plurality of compounds including a basic component and a catalyst component of impression compounds for application in a dental field comprising:
   a) at least one frame;
   b) at least two cartridges, disposed on said at least one frame;

c) a plunger-cylinder unit disposed in said frame and comprising:
   i) at least two punches displaceably supported in said at least one frame and coupled to said at least two cartridges wherein said at least two punches are actuated independently of each other, and wherein said at least two punches have a same length but different diameters supported in parallel with each other and are displaceable by said plunger-cylinder unit; and
   ii) at least one plunger coupled to at least one of said at least two punches for providing pressure to said at least one of said at least two punches;
d) a hydraulic system for actuating said at least one plunger and said at least one punch;
e) at least one pump coupled to said frame and in fluid communication with said plunger-cylinder unit; and
f) a motor coupled to said pump wherein said pump is driven by said motor;
h) at least one supply container in communication with said at least one pump wherein said hydraulic system actuates said at least one pump to cause fluid from said supply container to flow into said at least one plunger to cause said at least one plunger to drive at least one of said at least two punches to dispense said plurality of compounds.

* * * * *